US00PP27319P3

(12) United States Plant Patent
MacIlvaine et al.

(10) Patent No.: US PP27,319 P3
(45) Date of Patent: Nov. 1, 2016

(54) PISTACHIO ROOTSTOCK TREE NAMED WONDERFUL PISTACHIO ROOTSTOCK #4

(50) Latin Name: *Pistacia atlantica×P. integerrima*
Varietal Denomination: Wonderful Pistacia Rootstock #4

(71) Applicant: Wonderful Orchards LLC, Shafter, CA (US)

(72) Inventors: Joseph MacIlvaine, Bakersfield, CA (US); Eric Mercure, Bakersfield, CA (US); John Etchamendy, Wasco, CA (US)

(73) Assignee: Wonderful Orchards LLC, Shafter, CA (US)

( * ) Notice: Subject to any disclaimer, the term of this patent is extended or adjusted under 35 U.S.C. 154(b) by 83 days.

(21) Appl. No.: 14/544,204

(22) Filed: Dec. 9, 2014

(65) Prior Publication Data

US 2016/0165772 P1 Jun. 9, 2016

(51) Int. Cl.
*A01H 5/00* (2006.01)

(52) U.S. Cl.
USPC ..... Plt./152

(58) Field of Classification Search
USPC ..... Plt./174, 152
See application file for complete search history.

*Primary Examiner* — Annette Para
(74) *Attorney, Agent, or Firm* — Knobbe, Martens, Olson & Bear, LLP

(57) ABSTRACT

A new and distinct variety of pistachio tree, cv. Paramount Pistachio Rootstock #4, is characterized by producing large leaves, reddish-green new foliage, and dark green mature foliage. The new variety is useful as a rootstock for commercial nut bearing pistachio varieties. A new and distinct variety of pistachio tree, cv. 'Wonderful Pistachio Rootstock #4', is characterized by producing large leaves, reddish-green new foliage, and dark green mature foliage. The new variety is useful as a rootstock for commercial nut bearing pistachio varieties.

3 Drawing Sheets

Latin name of the genus and species claimed: *Pistacia atlantica×P. integerrima.*

Variety denomination: 'WONDERFUL PISTACHIO ROOTSTOCK #4'.

BACKGROUND AND SUMMARY OF THE INVENTION

This invention relates to the discovery and asexual propagation of a new and distinct variety of Pistachio tree, *Pistachio atlantica* (unpatented)×*P. integerrima* (unpatented), cv. 'Wonderful Pistachio Rootstock #4' as herein described and illustrated. The new variety was first selected as breeder number 'SR412-5'. The new variety is a hybrid of *P. atlantica* and *P. integerrima* which was first discovered on cultivated land from trees grown from seed produced by a cross of the two parent varieties. The new variety was discovered, further characterized, and propagated by Joe MacIlvaine, Eric Mercure and John Etchamendy in the San Joaquin Valley, Kern County, Calif.

The new variety 'Wonderful Pistachio Rootstock #4' is characterized by producing large leaves, reddish-green new foliage, dark green mature foliage and upright habits with rounded crown. The new variety is useful as a rootstock to nut bearing pistachio.

The male parent is *P. integerrima* (unpatented) and the female parent is *P. atlantica* (unpatented). The date of first planting was 1996, and the date of first flowering was 2000.

The new variety 'Wonderful Pistachio Rootstock #4' was first asexually propagated in 2013 by Eric Mercure by tissue culture in the Southern San Joaquin Valley in Kern County, Calif. and established and transmitted through succeeding propagation by air-layering.

The new variety 'Wonderful Pistachio Rootstock #4' differs from its male parent *P. integerrima* in that the leaves and leaflets are shorter. Also, the leaflet base is more rounded in the new variety. In addition, the leaves are less red when emerging and fall off sooner.

The new variety 'Wonderful Pistachio Rootstock #4' differs from its female parent *P. atlantica* in that new variety is more vigorous and is believed to be more resistant to verticillium disease. The leaflets of the new variety are smaller and less rounded with a faster growth rate. The new variety has an overall larger size canopy.

The new variety can be distinguished from other available varieties by its yield characteristics. The closest available varieties are Integerrima "Pioneer Gold" and UCB1, an *atlantica×integerrima* hybrid. Yields on *P. vera* have been observed to be consistently higher on mature trees on the new rootstock variety when compared to Pioneer Gold and UCB1. The new variety 'Wonderful Pistachio Rootstock #4' has a 65% improved yield over the average yield from *P. vera* on UCB1. The yield of the new variety 'Wonderful Pistachio Rootstock #4' was measured from 2004-2013.

The new variety 'Wonderful Pistachio Rootstock #4' can also be distinguished from "Pioneer Gold" by the leaf shape.

The new 'Wonderful Pistachio Rootstock #4' has been shown to maintain its distinguishing characteristics through successive asexual propagations by, for example, tissue culture and air layering.

Variations of the usual magnitude from the characteristics described herein may occur with changes in growing conditions, irrigation, fertilization, pruning, management and with climatic variation.

BRIEF DESCRIPTION OF THE DRAWINGS

The accompanying color photographic illustration

DETAILED DESCRIPTION OF THE PREFERRED EMBODIMENT

Figure 1:
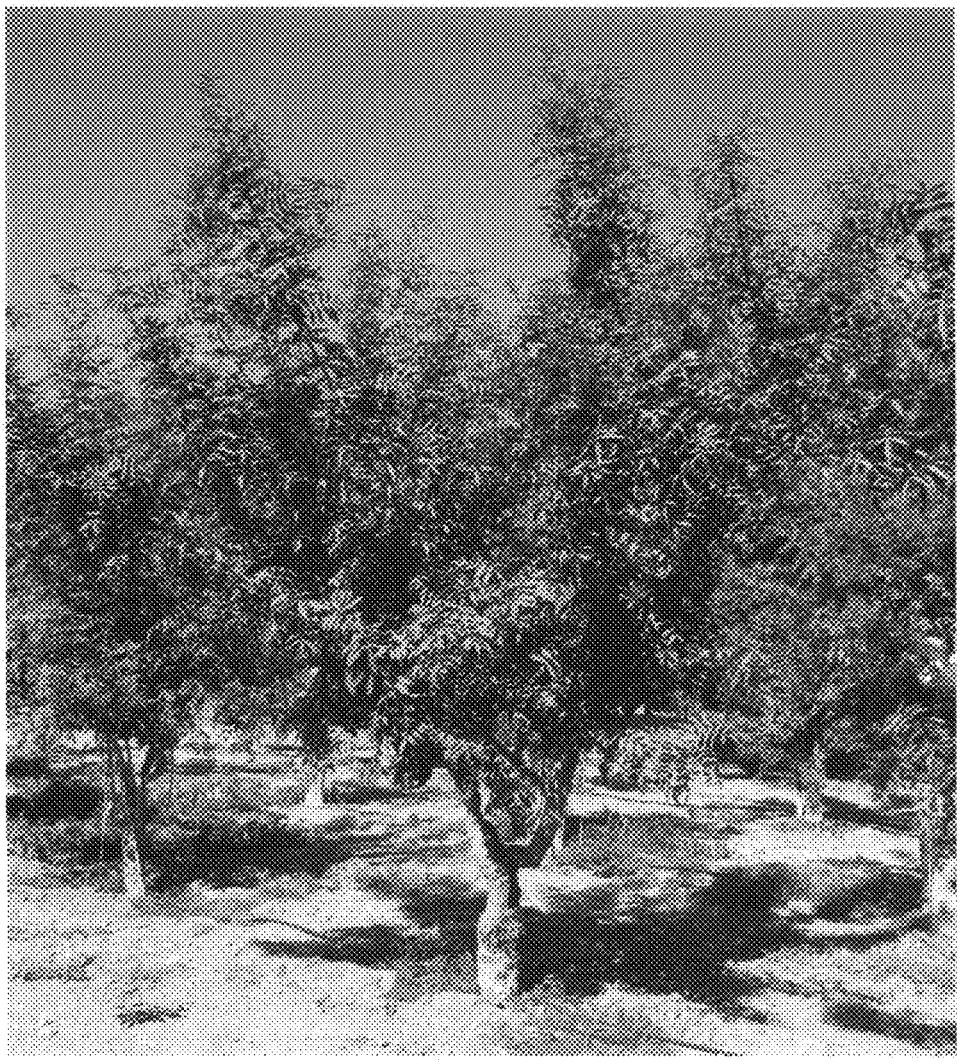
FIG. 1 shows a mature tree, with foliage, of the new variety 'Wonderful Pistachio Rootstock #4'.
Figure 2:
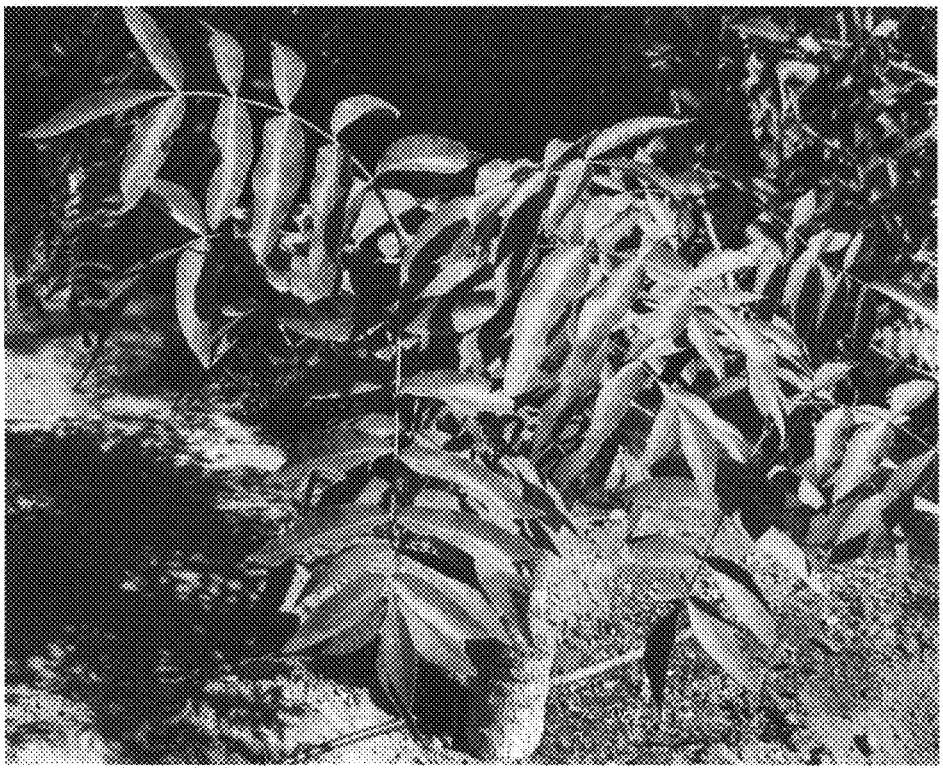
FIGS. 2 and 3 show a close up of the foliage. The colors of photographic illustration are as nearly true as is reasonably possible in a color representation of this type.
Figure 3:
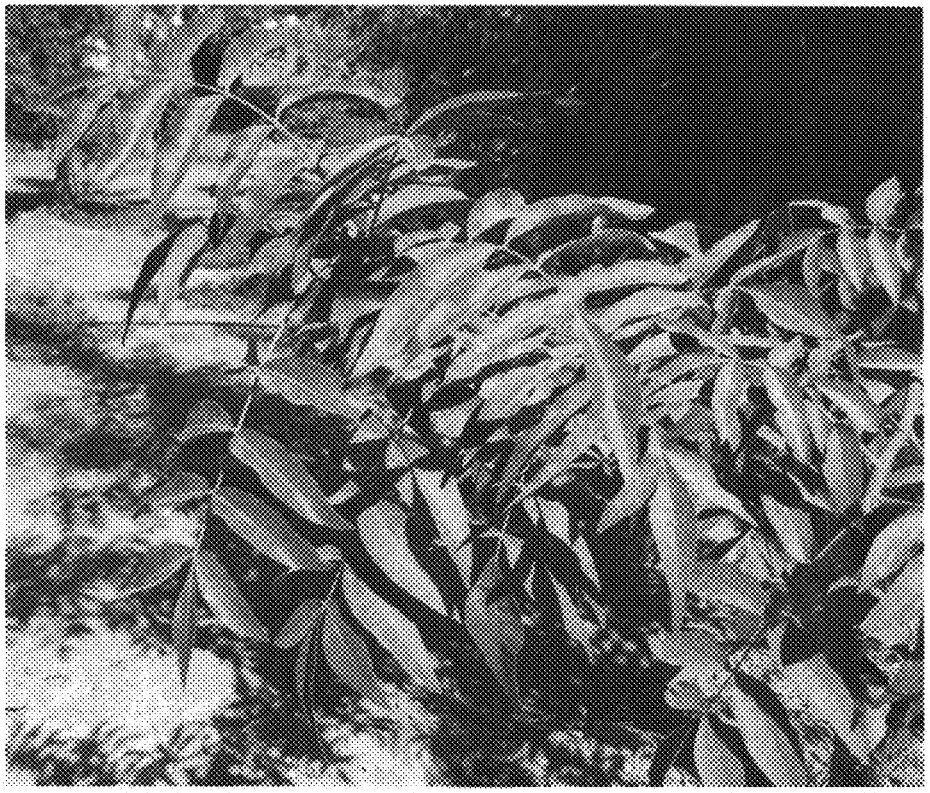

Throughout this specification, color names beginning with a small letter signify that the name of that color, as used in common speech, is aptly descriptive. Color names beginning with a capital letter designate values based upon The R.H.S. Colour Chart, published by The Royal Horticultural Society, London, England, 5$^{th}$ edition, 2007.

The descriptive matter which follows pertains to 'Wonderful Pistachio Rootstock #4' grown in the vicinity of the Southern San Joaquin Valley in Ken County, Calif. during 2002 to present, and is believed to apply to plants of the variety grown under similar conditions of soil and climate elsewhere.

PLANT

General:

*Growth*.—Upright tree with a rounded crown reaching 70-100 feet in height.

FOLIAGE

Leaves:

*Number of leaflets*.—7-9.

*Average length*.—Long, approximately 8-10 inches.

*Average width*.—Medium, approximately 5-6 inches.

Leaflets:

*Size*.—Medium, approximately 3 inches.

*Shape*.—Lanceolate.

*Length*.—Medium, approximately 2.5-3 inches.

*Color of new leaflets*.—About Dark Greyed-purple 183B.

*Color of old leaflets*.—About Dark Green 137A, Dark Green 137B and Yellow-Green 147B.

*Edge*.—Entire.

*Petiole*.—Petiolated.

*Arrangement of petiole*.—Pinnately compound.

*Arrangement of stems*.—Opposite.

*Shape of leaf at apex*.—Acuminate.

*Shape of leaf at base*.—Acute.

*Margin*.—Entire.

*Venation*.—Pinnate.

*Vein color*.—About Dark Green 137A, Dark Green 137B and Yellow-Green 147B.

*Texture of top surface*.—Globrous.

*Texture of bottom of surface*.—Globrous.

Ribs:

*Length*.—Approximately 6-8 inches.

*Color*.—About Dark Greyed-Purple 183A-B to Medium Yellow-Green 144A-B, and underside color About Medium Yellow-Green 144B.

Petiole:

*Length*.—Approximately 2 inches.

*Color*.—About Dark Greyed-Purple 183B to Medium Yellow-Green 144A-B.

*Diameter*.—Less than ⅛ inch.

Growth:

*Trunk shape*.—Upright.

*Trunk color*.—About Dark Brown 200B with fissures About Medium Grey-Brown 199D.

*Tree height*.—Approximately 4-5 feet prior to budding of the nut producing scion in July-September.

*Tree spread*.—None, as the rootstock is grown as a single stem.

*Trunk diameter*.—Large, approximately ½ to ¾ inches prior to budding. Diameter at the time of maturity is unknown.

*Bark texture*.—Striated when young and slightly furrowed with age.

*Vegetative bud size*.—Approximately ⅛ "-¼.

*Vegetative bud color*.—Reddish-gray.

What is claimed is:

1. A new and distinct variety of pistachio tree as herein illustrated and described.

* * * * *